United States Patent [19]
Newman

[11] 4,352,429
[45] Oct. 5, 1982

[54] MEANS FOR THE STORAGE AND ASEPTIC DELIVERY OF STERILIZED ARTICLES

[75] Inventor: Charles L. Newman, St. Paul, Minn.

[73] Assignee: Minnesota Mining and Manufacturing Company, St. Paul, Minn.

[21] Appl. No.: 168,501

[22] Filed: Jul. 14, 1980

Related U.S. Application Data

[63] Continuation of Ser. No. 20,440, Mar. 14, 1979, abandoned.

[51] Int. Cl.³ .................. A61B 19/02; A61L 15/00
[52] U.S. Cl. ................................................ 206/439
[58] Field of Search .............. 206/439, 438, 440, 363, 206/486

[56] References Cited

U.S. PATENT DOCUMENTS

| | | | |
|---|---|---|---|
| 2,897,962 | 8/1959 | Zackheim | 206/486 |
| 3,062,371 | 11/1962 | Patience | 206/440 |
| 3,527,400 | 9/1970 | Shepherd | 206/363 |
| 3,618,756 | 11/1971 | Trewella | 206/438 |

Primary Examiner—Herbert F. Ross
Attorney, Agent, or Firm—Cruzan Alexander; Donald M. Sell; Gary L. Griswold

[57] ABSTRACT

A package comprised of a first wall member adhered to a second wall member to form a storage zone with the first wall member having a window surrounded by border portions. The window and border portions are covered with a peelable flap member which protects the border portion after sterilization of the package so that an article placed within the package can be removed in a sterile condition.

4 Claims, 3 Drawing Figures

MEANS FOR THE STORAGE AND ASEPTIC DELIVERY OF STERILIZED ARTICLES

This is a continuation, application Ser. No. 20,440 filed Mar. 14, 1979 now abandoned.

This invention relates to packages for sterile articles and more particularly to a package of the type which avoids contamination of the article when it is removed from the package.

Various packages have been developed for aseptic delivery of articles into the sterile surgical environment. Ideally, the package may be easily opened and the previously sterilized article therein presented into the desired sterile field with minimum manipulation.

A package which generally exemplifies the prior art approach is disclosed in U.S. Pat. No. 3,754,700. This package allows a sterile article to be removed by peeling apart two previously adhered walls. Although the package is easily opened it has been found that the article contained therein may be contaminated in two ways. First, if the item placed inside the pouch formed by the two walls is of substantial bulk or weight, e.g., surgical drape, the item's own weight will be directed onto the peelable seal causing the seal to rupture during the rigors of shipment and handling, thus allowing contamination. Second, after opening the package, if great care is not utilized, the article exiting the package may contact an unsterile edge of the package.

In U.S. Pat. No. 4,057,144 still another package is disclosed which attempts to provide total aseptic delivery. This package is formed from a flexible tube having overlapping layers and a longitudinally extending strip bonded over the overlapping areas. A disadvantage of such a package is that of the numerous non-mating edges which result from the overlapping relationship, create a great likelihood that during the sealing of the ends of the flexible tube small passages will be formed through which contaminants may pass.

The package according to the present invention overcomes the above stated deficiencies of the prior art packages by providing a package by which, with minimum manipulation, channeled delivery of an article into the surgical environment in an aseptic condition can occur. The package of the present invention is comprised of a first wall and a second wall member which are joined together to form a storage space. The first wall member has a top edge, bottom edge, opposite side edges flanking the top edge and a window spaced from these edges which results in border portions between the edges and the window. The second wall member is joined to the first wall member by a primary seal along three of the edges of the first wall member. This primary seal is of sufficient strength to withstand the stresses produced by the weight and/or bulk of the article placed in the storage space.

The package is further comprised of a flap member attached to the bottom edge of the first wall member. The flap member overlays the window and border portions and its remaining unattached edges are peelably sealed to the external surface of the first member around the border portions.

After a surgical article is placed into the storage space, the top edge of the first wall member is sealed to the second wall member. The sealed package is sterilized.

When the sterilized article is desired, the flap member can be peeled from the first member whereby the article passes from the storage space through the window contacting only the sterile border portions which were previously protected by the flap member.

DESCRIPTION OF THE PREFERRED EMBODIMENTS

Figure 1:
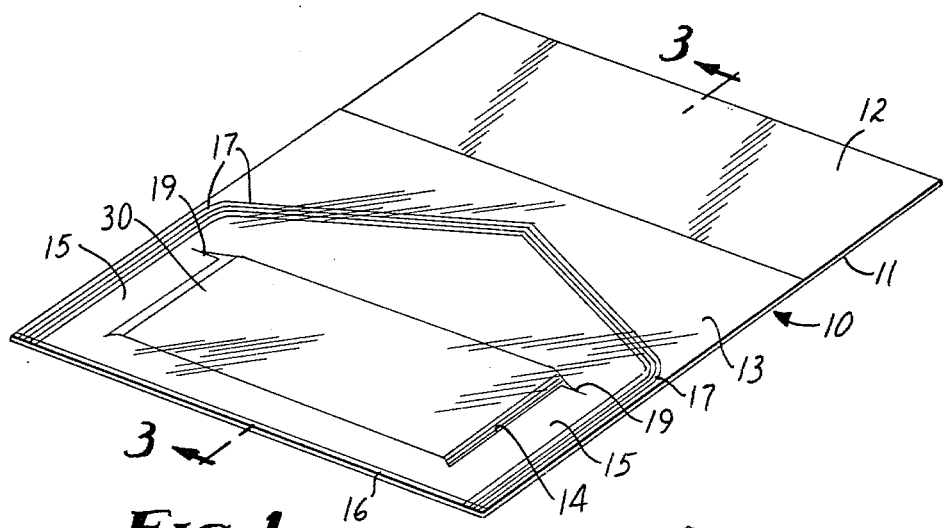
FIG. 1 is a perspective view of the package according to the present invention with a folded surgical drape contained therein.
Figure 2:
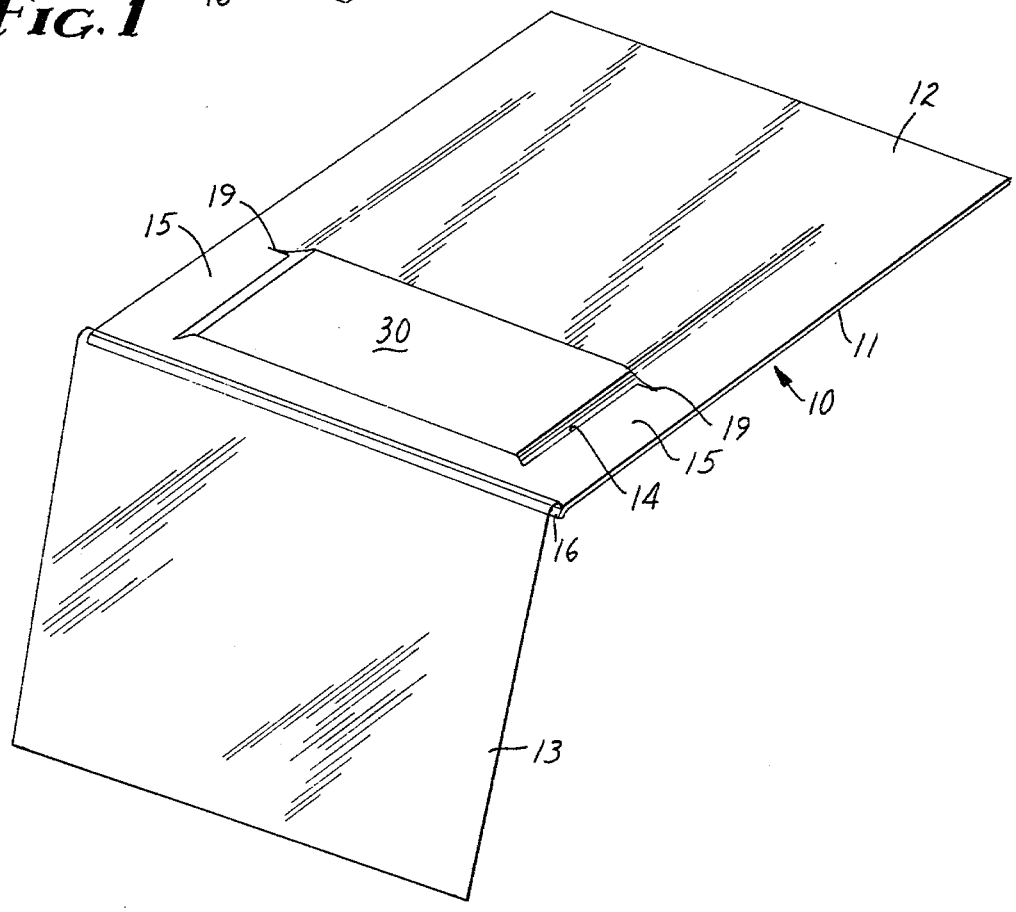
FIG. 2 is a perspective view of an open package in accordance with the present invention having a folded surgical drape contained therein.
Figure 3:
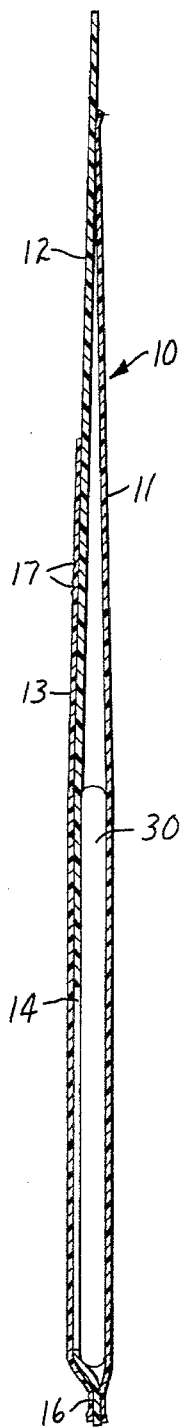
FIG. 3 is an enlarged cross-sectional view of the package according to the present invention taken through line 3—3 of FIG. 1.

Referring now to the drawings and more particularly to FIGS. 1, 2 and 3, there is shown a surgical pouch or package 10 containing a folded surgical drape 30. The package is comprised generally of a first wall member 12, a second wall member 11 and a flap member 13. The first wall member 12 is joined to the second wall member 11 along their opposite side and bottom edges to afford a storage space, e.g., a pouch.

The wall members 11 and 12 and flap member 13 should be made of a material which is sterilizable while at the same time being substantially impervious to dust and bacteria. The choice of materials is largely dependent on the method of sterilization to which the package 10 will be subjected. The sterilization methods most commonly used are gas (e.g., ethylene oxide), ionizing radiation or steam. If steam sterilization is utilized, the preferred material for the the first wall member 12 is surgical grade kraft paper with the flap and second wall member 11 being made of films which are autoclavable, e.g., nylon. When the ionizing radiation is used the wall and flap members are made of polymeric films which are stable to ionizing radiation.

Package 10, as depicted in FIG. 1, is designed for use in gas sterilization. The first wall member 12 is preferably made of Tyvek TM (a registered trademark of the DuPont Company of Wilmington, Del.), a spun bonded polyethylene. The second wall member 11 and flap member 13 are made from a transparent heat sealed polyester film, e.g., Scotch Pac, a trademark product of the 3M Company of St. Paul, Minn. or other appropriate thermoplastic film, e.g., polyolefin. The use of the transparent film allows the visual confirmation of the content of the package 10 prior to opening.

The first wall member 12 and second member 11 may be joined together by a primary seal. This primary seal which joins the bottom edge and opposite side edges of the first wall member to second wall member 11 may be made in any manner which provides for a seal which is both (1) capable of carrying the stresses produced by the weight of the article to be placed in the storage zone and (2) provides a bacteria and dust free seal which is capable of withstanding sterilization temperatures and pressures without loss of the integrity of the seal. The strength of the seal varies according to the item placed within the package 10. For the embodiment shown, the preferred range for the peel of the two wall members 11 and 12 is between 1.0 lb/in crossline to the delamination or the tearing of the materials.

Figure 4:
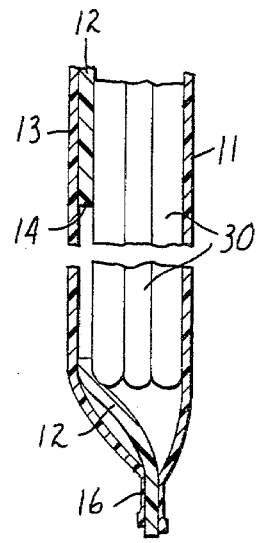
FIG. 4 is an enlarged fragmentary cross-sectional view of the lower portion of the package having a folded surgical drape contained therein (not to scale)
Figure 5:
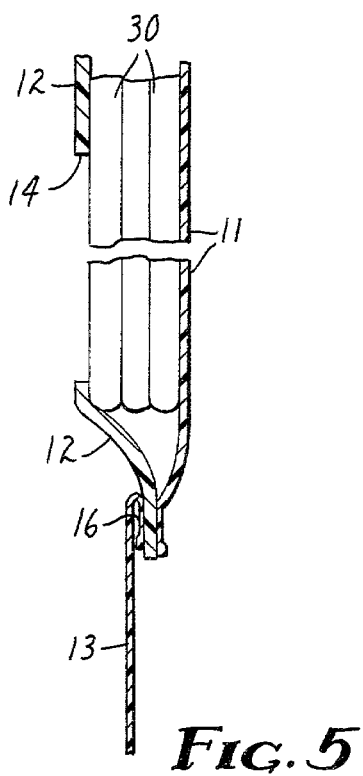
FIG. 5 is an enlarged fragmentary cross-sectional view of the lower portion of a opened package containing a folded surgical drape (not to scale)

The first wall member 12 is further comprised of a window 14. The dimensions of window 14 are largely dependent on the article which is to be placed in the storage space of package 10. The ultimate position of window 14 is also dependent on the article 30. In most cases it is preferred that window 14 be positioned in the first wall member such that it is spaced from the side edges to provide a border portions 15. Package depicted in the drawings is designed for use with the folded surgical drape 30. The window 14 is preferably positioned at the lower end of the first wall member 12. As seen in FIGS. 3, 4 and 5, when the package 10 is in a vertical position, the weight of surgical drape 30 is distributed on the second wall member 12, the first wall member 11 and the primary seal which joins these members. As seen in FIGS. 4 and 5, the portion of first wall member 12 above and below window 14 keeps the weight of the article 30 from being directed outside window 14 to the flap member 13, which is as discussed below, sealed to the first wall member 12 in manner which allow it to be peeled.

Figure 6:
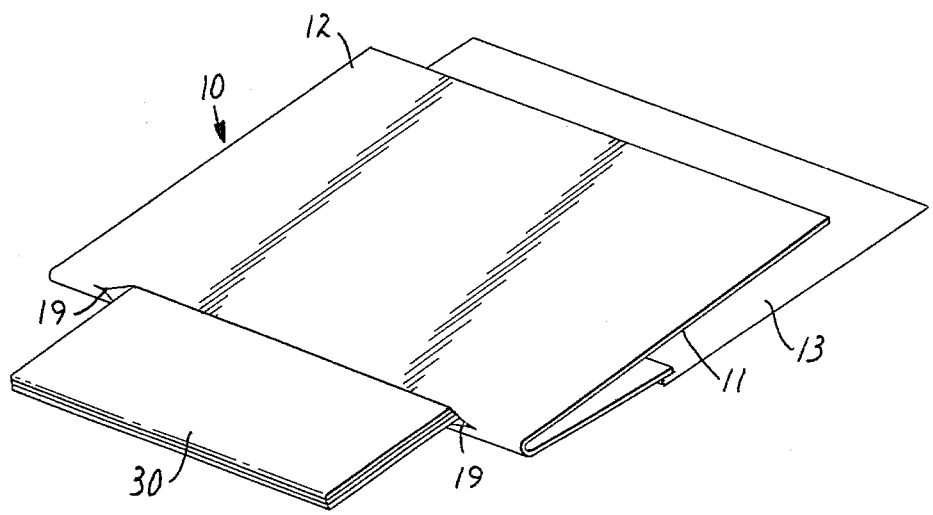
FIG. 6 is a perspective view of the package according to the present invention opened for aseptic delivery of the surgical drape.
Figure 7:
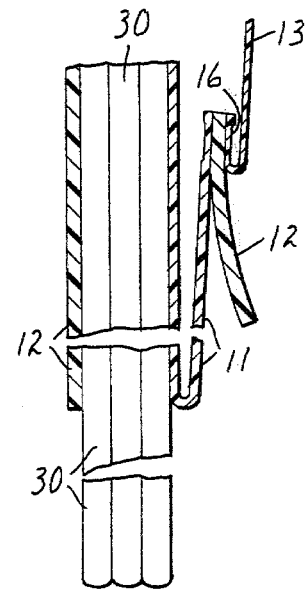
FIG. 7 is an enlarged fragmentary cross-sectional view of the lower portion of the opened package depicted in FIG. 6 (not to scale).

The first wall member 12 is also comprised of crease line slits 19 projecting from the upper corners of window 14 into the border portions toward the opposite side edges of the first wall member 12. Slits 19 act to create at fold line to control the distance which the first wall member 12 travels during the opening of package 10 (FIGS. 6 and 7).

The flap member 13 is positioned over the window 14 and border portion 15 and strippably joined to the first wall member 12 by a peelable seal 17. Peelable seal 17 may be formed in any desired manner which provides a positive, semipermanent bacteria and dust free seal which is capable of withstanding sterilization temperatures without loss of integrity. The strength of peelable seal 17 will vary according to the material used in package 10. In the present embodiment, seal 17 is made by combination of heat and pressure, i.e. heat seal. The range that is preferred for the present embodiment is from about 0.5 lb/inch crossline to about 3.0 lbs/inch. The upper portion of the seal 17 is made in the form of an inverted V. The inverted V allows the unattached upper portions of flap member 13 to be grasped to initiate the peeling of flap member 13.

The lower portion of flap member 13 is joined to first wall member 12 by seal 16 be made in a manner that results in the lower portion of flap member 13 being permanently affixed to second wall member 12. Alternatively it is contemplated that due to the accumulated crossline resistance along seal 16, flap member 13 remains attached to the first wall member 12 when the normal peel force is applied when seal 16 is formed by a method similar that of pealable seal 17. This attachment aids in the control of the movement of all wall members after the opening of the package. Moreover it is contemplated that flap member 13 and second wall member 11 be one piece of film folded over the lower edge of first wall member 12 and primarily sealed thereto.

In using package 10, the article 30 would be placed through the unsealed top. The top of package 10 would be sealed in a manner similar to previously sealed sides and bottom of wall members 11 and 12. The package 10 and contents would then be subjected to sterilization.

When the contents are needed, package 10 is grasped in one hand at the top of the jointure of the first wall and second wall members. The unattached upper edge of flap member 13 is grasped in the other hand. The flap member 13 is then peeled away from the second member 12 so as for the first time exposing the sterile border edges 15 and permitting access to the sterile article 30 through window 14. As best seen in FIGS. 2 and 5, the flap member 13 is peeled down to seal 16. The flap member is pulled in a direction perpendicular to package 10 to crease line slits 19. This results in the lower portion of the first wall member 12 being removed from its previously supportive (or occlusive) position (FIGS. 5 through 7) and the article 30 may exit package 10 contacting only the sterile border portion 15. The direction of folded surgical drape 30 exit may be further controlled by the width of window 14 acting in combination with a secondary seal which joins the first wall member and second wall member (not shown). These secondary seals are positioned such that they are both adjacent to window 14 and parallel to the side edges of first wall member 12. The secondary seal acts to limit the lateral movement of the article thereby ensuring that it will contact only the previously sterilized border portions.

What is claimed is:

1. A package having high strength, bacteria-impermeable, sterilizable wall members adapted to contain an article in a sterile condition for use in a surgical environment, said package comprising:
   (a) a first wall member having a top edge, bottom edge, opposite side edges flanking said top edge and having a window spaced from said edges to provide border portions between said edges and said window;
   (b) a second wall member being sealed to said first wall member to afford a storage space between said wall members adapted for containing said article; and
   (c) a flap member overlaying said window and said border portions and attached to said first wall member around the entire periphery of said window, said flap member being peelably sealed to said first wall member around said border portions so that when said flap member is peeled from said first member said article can pass from said storage space through said window while contacting only said border portions.

2. A package according to claim 1 wherein said second wall member and said flap member are one piece.

3. A package according to claim 1 wherein said first wall is sealed to said second wall member by a primary seal along the bottom edge, top edge and opposite side edges of said first wall member and a secondary confining of movement seal in the border portion parallel to the opposite side edges of said first wall member so that when said flap member is peeled from said first member said article can pass from said storage space through said window with limited lateral movement.

4. A package according to claim 3 wherein said first wall member further includes sites for controlling the travel of said first wall member during the passing of said article from said storage space, said slits being positioned adjacent said window and projecting toward the opposite edges of said first wall member.

* * * * *